US00PP16997P2

(12) United States Plant Patent
Brigante

(10) Patent No.: US PP16,997 P2
(45) Date of Patent: Aug. 15, 2006

(54) ***SAURURUS CHINENSIS* PLANT NAMED 'FLAMING DRAGON'**

(50) Latin Name: *Saururus chinensis*
Varietal Denomination: Flaming Dragon

(75) Inventor: David Brigante, Yamhill, OR (US)

(73) Assignee: E.F. Hughes, Inc., Tualatin, OR (US)

( * ) Notice: Subject to any disclaimer, the term of this patent is extended or adjusted under 35 U.S.C. 154(b) by 22 days.

(21) Appl. No.: 11/107,654

(22) Filed: Apr. 14, 2005

(51) Int. Cl.
*A01H 5/00* (2006.01)

(52) U.S. Cl. ..... Plt./263
(58) Field of Classification Search ..... Plt./263, Plt./342
See application file for complete search history.

*Primary Examiner*—Kent Bell
*Assistant Examiner*—June Hwu
(74) *Attorney, Agent, or Firm*—Klarquist Sparkman, LLP

(57) ABSTRACT

A new and distinct cultivar of *Saururus chinensis* plant characterized by gold, rather than green leaves.

1 Drawing Sheet

Botanical denomination: *Saururus chinensis*.
Variety designation: 'Flaming Dragon'.

The present invention relates to a new and distinct cultivar of *Saururus chinensis* plant and given the cultivar name of 'Flaming Dragon'. *Saururus chinensis* is in the family Saururaceae. *Saururus chinensis* 'Flaming Dragon' is a naturally occurring branch mutation of *Saururus chinensis*, an unnamed and unpatented plant. 'Flaming Dragon' was discovered in Tualatin, Oreg.

What makes this *Saururus chinensis* unique is the color of its leaves. They are a shocking gold when young and mature to a yellow green.

This new cultivar has been reproduced only by asexual propagation (tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

DETAILED PLANT DESCRIPTION

Figure 1:
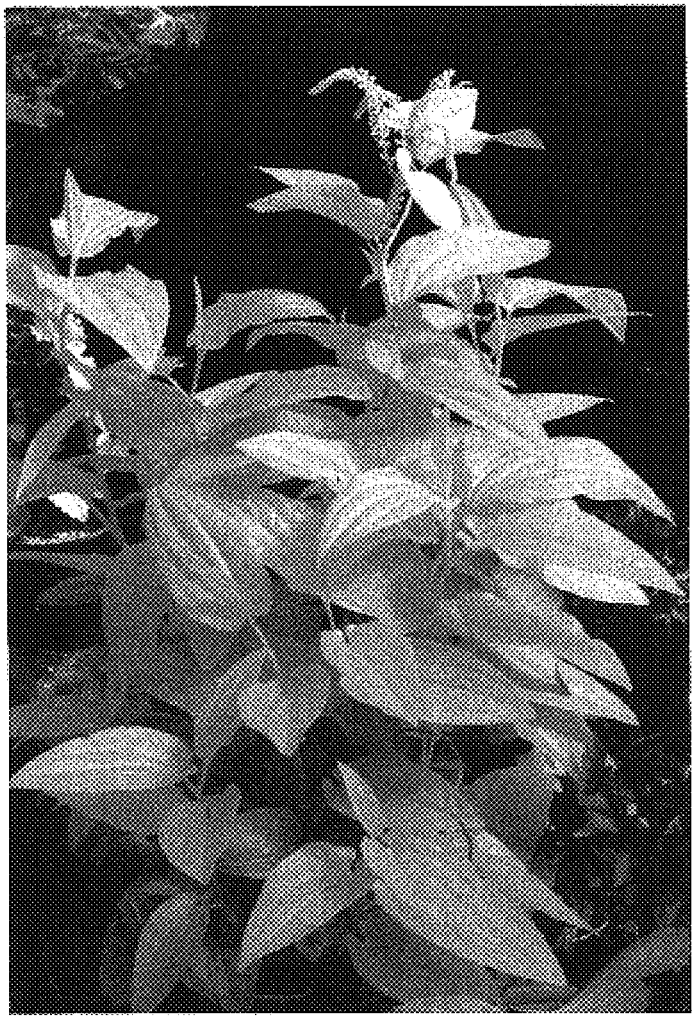
FIG. 1 shows *Saururus chinensis* 'Flaming Dragon' growing in a 2 gallon container in a warm greenhouse in late March in Canby, Oreg.
Figure 2:
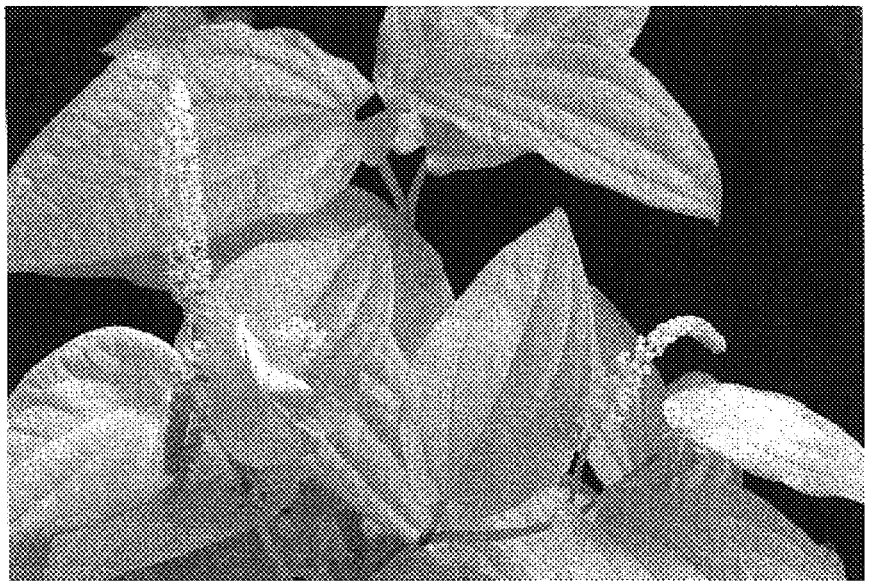
FIG 2 shows a close up of the flowers and new growth.

The following is a detailed description of the new *Saururus chinensis* cultivar based on observations of a two year old specimen grown in a two gallon container in a warm greenhouse in Canby, Oreg. This greenhouse is kept at 62 to 65 degrees F. minimum and 95 degrees F. highs. The color descriptions are all based on The Royal Horticultural Society Colour Chart.

Plant:
- *Form.*—Rhizomatous, herbaceous perennial.
- *Hardiness.*—USDA Zone 6 to 9.

- *Culture.*—Part shade, grows as a terrestrial in organic soils or as an aquatic in 6" of water.
- *Size.*—60 cm tall and 40 cm wide.
- *Habit.*—Erect, clump forming.
- *Roots.*—Narrow, coming off the rhizome nodes, tan, Grey Brown 199C. Roots grow easily from rhizome cuttings or divisions.

Rhizome: Thick, fleshy, White 155A, sheathed with tan, thin, papery, perfoliate stipule, Brown 200D. Grows to 5 mm wide.

Stem:
- *Number.*—7.
- *Size.*—14 to 17 cm long and up to 4 mm wide.
- *Color.*—Yellow Green 150C tinted darker with 152D, prominent nodes of young leaves are maroon, Greyed Purple 185B.
- *Vestiture.*—Glabrous.

Leaf:
- *Type.*—Simple.
- *Arrangement.*—Spiral.
- *Shape.*—Ovate.
- *Venation.*—5 main veins from the base, then reticulate.
- *Margins.*—Entire, undulate slightly.
- *Apex.*—Acute.
- *Base.*—Cordate.
- *Blade size.*—8.5 to 15 cm long and 5 to 7 cm wide.
- *Vestiture.*—Glabrous.
- *Surface.*—Glossy.
- *Texture.*—Thin, smooth.
- *Petiole.*—Clasps around the stem.
- *Petiole length.*—Changes from 4.5 cm at the bottom of the stem to 1 cm at the top.
- *Petiole vestiture.*—Glabrous.
- *Petiole color.*—Green 138B.
- *Leaf color.*—Topside — Young leaves, Yellow Green 151A. Mature leaves, Yellow Green 144A. Bottomside — Young leaves, between Greyed Yellow 160A and Yellow Green 152D. Mature leaves, Yellow Green 146C.

Inflorescence:
- *Type.*—Raceme on sides at end of stem.
- *Shape.*—Inflorescence is narrow and nodding in bud.
- *Number of flowers.*—75 per raceme.

*Size.*—Grows to 12 cm long and 12 mm wide.

*Bract.*—Subtending the base of each inflorescence, leaf like, 4.4 to 7 cm long and 3 to 4.5 cm wide, colored white in an overlay over the gold, whitest at the base (White 155B) and gold at the tips (Yellow Green 151A).

*Pedicel.*—White 155B, 3 mm long, pubescent, curve upward when in fruit.

*Bloom period.*—Spring in Canby, Oreg.

Flower bud:

*Color.*—Yellow Green 154C to Yellow 4C.

*Shape.*—Round, cauliflower-like.

*Size.*—1.8 mm.

Flower:

*Type.*—Incomplete, no calyx or corolla.

*Size.*—1.8 mm wide and deep.

*Color of stamen and pistil.*—*White* 155A.

*Stamen number.*—5 .

*Pollen color.*—Cream, Yellow 4D.

*Fragrance.*—Sweet.

*Lastingness.*—Each flower lasts for about 4 days on the plant.

Fruit: Round, warty, one seeded.

Seed: Not seen. Assumed to be the same as the species.

Diseases and pests: No diseases found of this new variety. All *Saururus chinensis* are susceptible to snails and slugs.

COMPARISON TO SIMILAR *SAURURUS CHINENSIS*

Compared to *Saururus chinensis* (an unpatented plant), *Saururus chinensis* 'Flaming Dragon' has gold, rather than green leaves.

I claim:

1. A new and distinct *Saururus chinensis* plant as substantially illustrated and described.

* * * * *